(12) United States Patent
Klassen et al.

(10) Patent No.: US 12,033,404 B2
(45) Date of Patent: Jul. 9, 2024

(54) INCIDENTAL FINDING AUGMENTATION SYSTEM FOR MEDICAL RADIOLOGY

(71) Applicant: KONINKLIJKE PHILIPS N.V., Eindhoven (NL)

(72) Inventors: Prescott Peter Klassen, Cambridge, MA (US); Lyubomir Georgiev Zagorchev, Burlington, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 819 days.

(21) Appl. No.: 16/982,749

(22) PCT Filed: Mar. 20, 2019

(86) PCT No.: PCT/EP2019/056904
§ 371 (c)(1),
(2) Date: Sep. 21, 2020

(87) PCT Pub. No.: WO2019/180056
PCT Pub. Date: Sep. 26, 2019

(65) Prior Publication Data
US 2021/0004624 A1 Jan. 7, 2021

Related U.S. Application Data

(60) Provisional application No. 62/645,925, filed on Mar. 21, 2018.

(51) Int. Cl.
*G06T 7/00* (2017.01)
*G06T 7/11* (2017.01)
(Continued)

(52) U.S. Cl.
CPC ............ *G06V 20/62* (2022.01); *G16H 30/20* (2018.01); *G16H 30/40* (2018.01)

(58) Field of Classification Search
USPC .......... 382/128–224; 378/21–50; 704/1–275; 128/915–916, 920–925
See application file for complete search history.

(56) References Cited

U.S. PATENT DOCUMENTS 9,081,877 B2 * 7/2015 Futami .................. G16H 30/40
9,256,951 B2 2/2016 Zagorchev
(Continued)

FOREIGN PATENT DOCUMENTS

WO WO2018026431 A1 2/2018
WO WO2019180120 A1 9/2019

OTHER PUBLICATIONS

Kubo, Takeshi, Information Processing Apparatus, Information Processing Method, and Information Processing System; Mar. 22, 2017 (Year: 2017).*
(Continued)

*Primary Examiner* — Marcellus J Augustin
(74) *Attorney, Agent, or Firm* — Sherry Austin

(57) ABSTRACT

Systems and methods for magnetic resonance (MR) examination are provided. In an embodiment, a method for MR examination includes receiving, at a computing device in communication with a magnetic resonance imaging (MRI) device, MR data of a patient body comprising a plurality of anatomical structures, the plurality of anatomical structures including a region of interest, segmenting, by the computing device, the MR data to obtain geometries of the plurality of anatomical structures, receiving, at the computing device, a report comprising text descriptions representative of the plurality of anatomical structures, associating, by the computing device, the text descriptions with respective geometries of the plurality of anatomical structures, identifying, by the computing device, the text descriptions associated with anatomical structures within or outside of the region of interest; and outputting, by the computing device, a graphi-
(Continued)

cal representation based on the identified text descriptions associated with anatomical structures within or outside of the region of interest.

14 Claims, 9 Drawing Sheets

(51) Int. Cl.
    *G06V 20/62*     (2022.01)
    *G16H 30/20*     (2018.01)
    *G16H 30/40*     (2018.01)

(56) References Cited

U.S. PATENT DOCUMENTS

| | | | | |
|---|---|---|---|---|
| 10,140,421 | B1* | 11/2018 | Bernard | A61B 6/563 |
| 2004/0181431 | A1* | 9/2004 | Kuth | G16H 15/00 705/2 |
| 2012/0283546 | A1* | 11/2012 | Zuehlsdorff | A61B 6/5217 600/407 |
| 2015/0146951 | A1 | 5/2015 | Zagorchev | |
| 2016/0086326 | A1* | 3/2016 | Raschke | G06T 7/11 382/131 |
| 2020/0286232 | A1* | 9/2020 | Enzmann | G06T 7/143 |

OTHER PUBLICATIONS

Gao Dashan, Computer-Aided Diagnosis System for Medical Images Using Deep Convolutional Neural Networks; Feb. 8, 2018 (Year: 2018).*

PCT International Search Report, International application No. PCT/EP2019/056904, dated Jun. 24, 2019.

Zagorchev L. et al., "Evaluation of Traumatic Brain Injury Patients Using a Shape-Constrained Deformable Model", MBIA'11: Proceedings of the First International Conference on Multimodal Brain Image Analysis, Sep. 18, 2011. Proceedings (vol. 7012 pp. 118-125) 2011.

* cited by examiner

| Regions outside ROE | Report findings | Alert | % of concurrence | Recommended actions |
|---|---|---|---|---|
| Anatomy A: | Description I | | | |
| Anatomy B: | Description II | Possible actionable | 80% | Action 1 |
| Anatomy C: | Normal | | | |
| Anatomy D: | Normal | | | |
| Anatomy E: | Description III | | | |
| Anatomy F: | Normal | | | |
| Anatomy G: | Description IV | | | |
| Anatomy H: | Normal | | | |
| Anatomy I: | Normal | | | |
| Anatomy J: | Description V | | | |
| Anatomy K: | Description VI | Possible actionable | 75% | Action 2 |
| Anatomy L: | Description VII | | | |
| Anatomy M: | N/A | | | |
| Anatomy N: | N/A | | | |
| Anatomy O: | N/A | Possible actionable | 60% | Action 3 |
| Anatomy P: | N/A | | | |

INCIDENTAL FINDING AUGMENTATION SYSTEM FOR MEDICAL RADIOLOGY

CROSS-REFERENCE TO RELATED APPLICATIONS

This patent application claims the priority benefit under 35 U.S.C. § 371 of International Patent Application no. PCT/EP2019/056904, filed Mar. 20, 2019, which also claims the priority benefit under 35 U.S.C. § 119(e) of U.S. Provisional Application No. 62/645,925 filed on Mar. 21, 2018, the contents of which are herein incorporated by reference.

TECHNICAL FIELD

The present disclosure relates generally to radiological examination, and in particular, to systems and methods for augmenting radiology report findings that are outside the region concerning the reason of examination.

BACKGROUND

After a physician interviewed and conducted preliminary examination of a patient, the physician may conclude that a radiological scan of a region of the patient's body should be ordered for accurate diagnosis. This region of the patient's body is sometimes referred to as a region of interest (ROI). In addition, as the ROI is or is about the very reason why the radiological scan is ordered, the ROI can also be referred to as the reason of examination (ROE). Once the radiology department receives an order of radiological scan from the physician, a radiologist performs a radiological scan on the patient, with a focus on the ROI/ROE. A radiological scan not only includes anatomical structures within the ROI/ROE, but also anatomical structure outside the ROI/ROE. Conventionally, a radiologist visually reviews the radiological images in search for physical anomalies both within and outside of the ROI/ROE. The ordering physician typically focuses only on the any anomaly findings within the ROI/ROE. Any findings outside the ROI/ROE are referred to as incidental findings as they are not representative of the ROI and ROE. In cases where the anomalies outside the ROI/ROE are actionable, the radiologist may not communication them to the ordering physician and/or an ordering physician may not focus on them because they are outside the ROI/ROE. If the radiologist does not communicate the actionable finding or the physician does not act upon recommendations base on the findings, the patient may not receive appropriate follow-up and an observed condition might remain undiagnosed.

SUMMARY

Embodiments of the present disclosure provide methods and systems configured to augment incidental findings in a radiology report. A system according to the present disclosure includes a computing device in communication with a magnetic resonance imaging (MRI) device. The computing device can receive from the MRI device magnetic resonance (MR) data of a patient body. The patient body includes a plurality of anatomical structures and the plurality of anatomical structures includes a region of interest. The computing device can segment the MR data to obtain geometries of the plurality of anatomical structure. The computing device can also receive a radiology report that includes text descriptions representative of the plurality of anatomical structures. By associating the text descriptions with respective geometries of the plurality of anatomical structures, the computing device can identify the text descriptions associated with anatomical structures within or outside of the region of interest. The computing device is further operable to output a graphical representation based on the identified text descriptions associated with anatomical structures within or outside the region of interest.

Systems and methods for magnetic resonance (MR) examination are provided. In an embodiment, a method for MR examination includes receiving, at a computing device in communication with a magnetic resonance imaging (MRI) device, MR data of a patient body comprising a plurality of anatomical structures, the plurality of anatomical structures including a region of interest, segmenting, by the computing device, the MR data to obtain geometries of the plurality of anatomical structures, receiving, at the computing device, a report comprising text descriptions representative of the plurality of anatomical structures, associating, by the computing device, the text descriptions with respective geometries of the plurality of anatomical structures, identifying, by the computing device, the text descriptions associated with anatomical structures within or outside of the region of interest; and outputting, by the computing device, a graphical representation based on the identified text descriptions associated with anatomical structures within or outside of the region of interest. In some embodiments, the graphical representation includes highlighted boundaries of geometries of anatomical structures outside the region of interest.

In some embodiments, associating the text descriptions with respective geometries of the plurality of anatomical structures includes parsing the text descriptions. In some implementations, associating the text descriptions with respective geometries of the plurality of anatomical structures includes recognizing text in the report. In some embodiments, the text descriptions associated with the anatomical structures outside of the region of interest include an actionable finding associated with an anatomic structure outside the region of interest. In some embodiments, the method for MR examination further includes storing in a database the region of interest and the actionable finding associated with the anatomic structure outside the region of interest. In some embodiments, the method further includes obtaining, by accessing the database, a probability of concurrence of the actionable finding associated with the anatomic structure outside of the region of interest and the region of interest being so designated. In some instances, the graphical representation includes the probability of concurrence of the actionable finding associated with the anatomic structure outside of the region of interest and the region of interest being so designated. In some implementations, the graphical representation includes a recommendation of actions based on the probability of concurrence of the actionable finding associated with the anatomic structure outside of the region of interest and the region of interest being so designated.

In another embodiment, a magnetic resonance (MR) examination system includes a computing device in communication with a magnetic resonance imaging (MRI) device. The computing device is operable to receive, from the MRI device, MR data of a patient body comprising a plurality of anatomical structures, the plurality of anatomical structures including a region of interest, segment the MR data to obtain geometries of the plurality of anatomical structures, receive a report comprising text descriptions representative of the patient body, associate the text descriptions with respective geometries of the plurality of anatomical structures, identify the text descriptions associated with anatomical structures within or outside of the region of interest, and output, to a display device, a graphical representation based on the identified text descriptions associated with anatomical structures within or outside of the region of interest. In some embodiments, the MR examination system further includes the MRI device. In some embodiments, the MR examination system further includes the display device. In some implementations, the text descriptions associated with the anatomical structures outside of the region of interest include an actionable finding associated with an anatomic structure outside the region of interest. In some implementations, the computing device is further operable to store in a database the region of interest and the actionable finding associated with the anatomic structure outside the region of interest. In some embodiments, the computing device is further operable to obtain, by accessing the database, a probability of concurrence of the actionable finding associated with the anatomic structure outside of the region of interest and the region of interest being so designated. In some instances, the graphical representation includes the probability of concurrence of the actionable finding associated with the anatomic structure outside of the region of interest and the region of interest being so designated. In some embodiments, the graphical representation includes a recommendation of actions based on the probability of concurrence of the actionable finding associated with the anatomic structure outside of the region of interest and the region of interest being so designated.

Other devices, systems, and methods specifically configured to interface with such devices and/or implement such methods are also provided.

Additional aspects, features, and advantages of the present disclosure will become apparent from the following detailed description along with the drawings.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 9 is a table illustrating an exemplary graphical representation of augmented incidental findings, according to aspects of the present disclosure.

DETAILED DESCRIPTION

Figure 1:
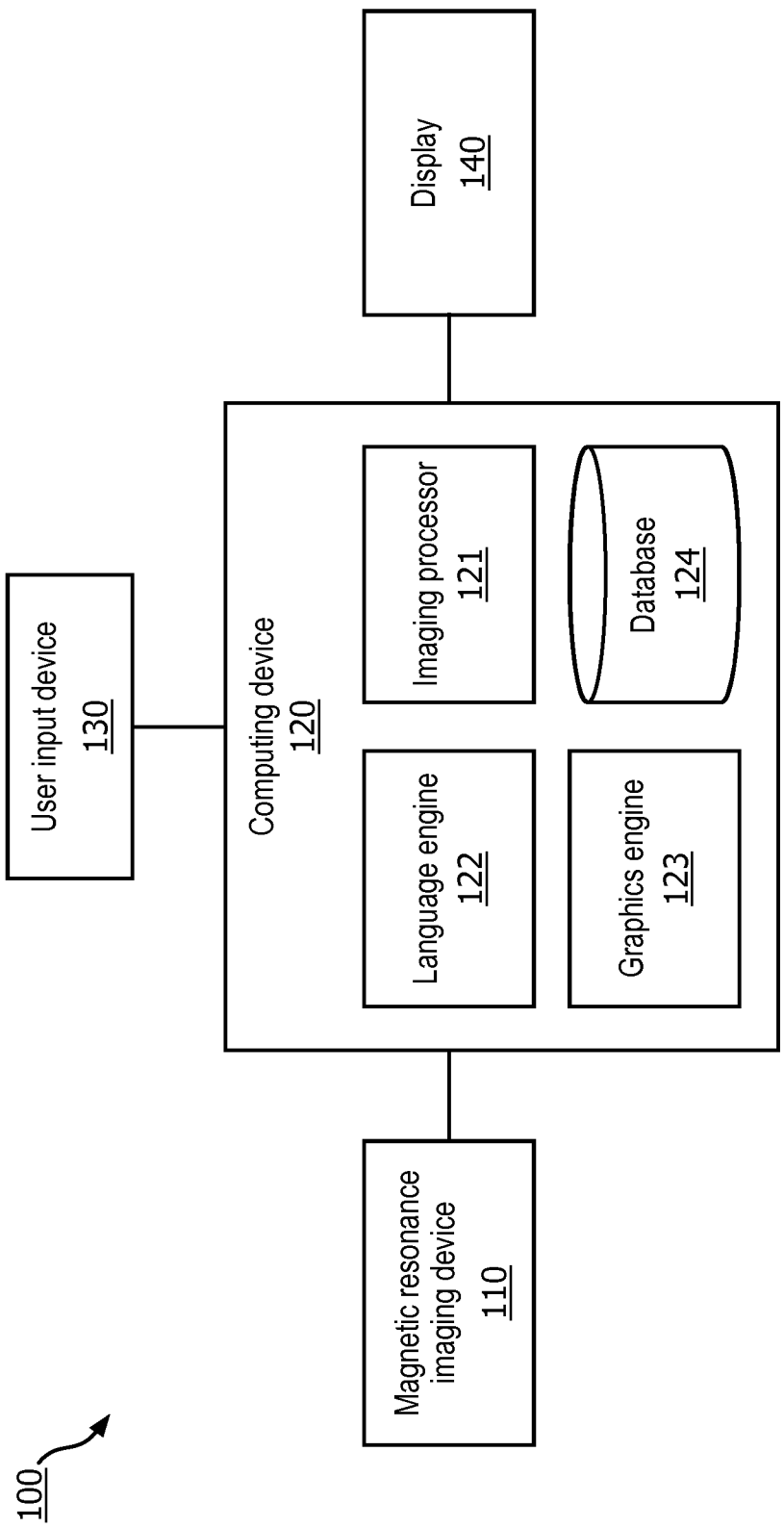
FIG. 1 is a schematic diagram of a system for MR examination, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates.

Referring now to FIG. 1, shown therein a schematic diagram of a system 100 for MR examination (can also be referred to as an MR examination system 100). The system 100 includes a computing device 120 connected to a magnetic resonance imaging (MRI) device 110, a user input device 130, and a display device 140. The computing device 120 includes an imaging processor 121, a language engine 122, a graphics engine 123 and a database 124. The computing device 120 can be a workstation or a controller that serves as an interface between the MRI device 110 and the display device 140. The user input device 130 serves as an interface between a user and the computing device 120 and allows the user to interact with the computing device 120 by entering user inputs. The user input device 130 can be a keyboard, a camera, a scanner, a mouse, a touchpad, a trackpad, a touchscreen mounted on the display device 140, a communication port, a USB port, a hand gesture control device, or a virtual reality glove.

The computing device 120 performs several functions. In some embodiments, the computing device 120 can receive magnetic resonance (MR) data from the MRI device 110, process the same by use of the imaging processor 121 and output MR image data to the display device 140 for display of the MR images. In some implementations, the imaging processor 121 of the computing device 120 can automatically segment anatomical structures in received MR data based on a segmentation protocol. In some instances, the imaging processor 121 can automatically segment the anatomic structures in the MR data based on a three-dimensional (3D) model of a brain or a patient body. In instances where the patient body includes a brain, the computing device 120 of the system 100 receives a 3D brain model from a storage media or through wired or wireless connection to a server or a remote workstation where the 3D brain model is stored. In some implementations, the 3D brain model can be stored in the database 124 or a storage device retrievable by the computing device 120. In some instances, the 3D brain model is a shape-constrained deformable brain model. In some instances, the 3D brain model may be the brain model described in "Evaluation of traumatic brain injury patients using a shape-constrained deformable model," by L. Zagorchev, C. Meyer, T. Stehle, R. Kneser, S. Young and J. Weese, 2011, in *Multimodal Brain Image Analysis* by Liu T., Shen D., Ibanez L., Tao X. (eds). MBIA 2011. *Lecture Notes in Computer Science*, vol 7012. Springer, Berlin, Heidelberg, the entirety of which is hereby incorporated by reference. In some instances, the 3D brain model may be the deformable brain model described in U.S. Pat. No. 9,256,951, titled "SYSTEM FOR RAPID AND ACCURATE QUANTITATIVE ASSESSMENT OF TRAUMATIC BRAIN INJURY" or the shape-constrained deformable brain model described in U.S. Pat. App. Pub. No. 20150146951, titled "METHOD AND SYSTEM FOR QUANTITATIVE EVALUATION OF IMAGE SEGMENTATION," each of which is hereby incorporated by reference in its entirety. By segmenting the anatomical structures in the MR data, the computing device 120 can obtain the geometries of these anatomical structures in the MR data by delineating boundaries of these anatomical structures.

In some embodiments, the computing device 120 can receive a region of interest (ROI). The ROI is a region of the patient body which the physician ordering the radiological scan or MR scan (sometimes referred to as the ordering physician) wishes to further examine for accurate diagnosis. Because the ROI is or is concerning the very reason of the radiological examination, the ROI can sometimes be referred to as the reason of examination (ROE). Throughout the present disclosure, ROI and ROE will be used interchangeably. In some instances, the ROI/ROE can be printed in a document, such as an order for radiological examination. In those instances, the image of the document can be captured by the user input device 130, such as a camera or a scanner. To identify the ROI/ROE, the image of the document can be analyzed by the language engine 122. In some embodiments, the language engine 122 can recognize the text in the image of the document. Once the text is recognized, the language engine 122 can parse the recognized text to identify the anatomical structure(s) corresponding to the ROI/ROE. The ROI/ROE can also be input into the computing device 120 using a different kind of the user input device 130. For example, a user or a radiologist can type in the ROI/ROE on a keyboard, or pick an ROI/ROE from a drop-down menu using a mouse, touchpad, trackpad, or a touchscreen. In some other instances, the ROI/ROE is stored on a USB drive and the ROI/ROE can be received by the computing device 120 when the USB drive is plugged into the USB port. In some other implementation, the ROI/ROE is stored on a database or a server, which is connected or connectable to the computing device 120 wirelessly or by wire via communication port. In those implementations, the computing device 120 can access the ROI/ROE stored in such a database or server. In situations where in the ROI/ROE is not captured from a document, no text recognition is necessary. The ROE/ROI can be analyzed by the language engine 122 to identify the anatomical structure(s) corresponding to the ROI/ROE.

In some embodiments, the computing device 120 can receive a radiology report prepared by a radiologist and analyze the radiology report by use of the language engine 122. The radiology report includes various findings and impressions of the radiologist after he or she examines the MR images that can be displayed on the display device 140. In addition, the radiology report can include anatomical structures that are within the ROI/ROE or outside the ROI/ROE. The radiology report can be a handwritten or computer generated hardcopy or a computer readable soft copy. In implementations where the radiology report is a hardcopy, the user input device 130 can be a camera or a scanner that captures an image of the hardcopy. The language engine 122 can operate to recognize the text in the captured image of the hardcopy and convert the same into a form readable by the language engine 122. The language engine 122 can then associate the computer-readable text descriptions with geometries of anatomical structures of the patient body. In implementations where the radiology report is a computer readable softcopy, the text recognition operation can be omitted. The computer readable text is then analyzed or parsed by the language engine 122 to identify text descriptions associated with anatomical structures of the patient. In some embodiments, the radiology report is generated by an interactive computer interface where the radiologist picks an anatomical structure from a pull-down list of selections and then chooses one or more findings from a pull-down list of selections. When the radiology report is generated through such an interactive computer interface, no text recognition or parsing operations are needed as the text descriptions are automatically associated with the selected anatomical structures.

In some embodiments, the computing device 120, by use of the language engine 122 or the imaging processor 121, can identify the text descriptions associated with anatomical structures within the ROI or outside the ROI. In some implementations, the computing device 120 will compare the anatomical structures mentioned in the radiology report with the one or more anatomical structures identified as corresponding to the ROI/ROE, to identify the out-of-ROI anatomical structures mentioned in the radiology report. By doing that, the computing device 120 can identify the text descriptions associated with the out-of-ROI anatomical structures and anatomical structures within the ROI/ROE.

In some embodiments, the database 124 of the computing device 120 stores historical and statistical data about ROE and incidental findings and/or anomalies. The historical and statistical data stored on the database 124 can be analyzed by the computing device 120 to identify probability of concurrence of actionable incidental findings and a given anatomical structure in the ROE. For example, if an ROE includes three anatomical structures, the computing device 120 can access the database 124 and determine the probability of concurrence of actionable incidental findings and each of the three anatomical structures in the ROE. In some implementations, the computing device 120 can also take into consideration gender, race, and age of the patient such that the determination of probable concurrence of actionable incidental findings/anomalies can be more accurate. In some other implementations, the computing device 120 can access the patient's historical data, if any, stored in the database 124 to determine patient-specific probabilities of actionable incidental findings/anomalies. It is noted that while the database 124 is depicted as an integrated element of the computing device 120, the database 124 can be a remote database or server connected to the computing device 120 by wire or wirelessly. In some embodiments, the database 124 can be cloud-based services provided by a third-party medical database service provider. In some instances, the computing device 120 can store the ROI/ROE and the incidental findings in the present radiology report in the database 124 for future references and analysis.

In some embodiments, the graphics engine 123 of the computing device 120 can generate a graphical representation of the incidental findings, including the text descriptions in the radiology report that are associated with anatomical structures outside the ROI/ROE. In some implementations, the graphical representation can include a list of anatomical structures outside the ROI/ROE and associated text descriptions. In some other implementations, the graphical representation can include a table of anatomical structures outside the ROI/ROE and associated text descriptions. In some embodiments, the graphical representation can include MR images where the boundaries of anatomical structures outside the ROI/ROE are highlighted to indicate incidental findings in the radiology report. In some other embodiments, the graphical representation can include an image of the radiology report and highlighted text descriptions associated with anatomical structures outside the ROI/ROE. In some instances, the graphics engine 123 can output the graphical representation to the display device 140 for display. In some embodiments, the graphical representation can further include the probability of concurrence of the ROI/ROE and actionable incidental findings.

In some embodiments, the system 100 can include radiology report validation features similar to those described in U.S. Patent Application No. 62/645,919, titled "Medical Radiology Report Validation and Augmentation System," filed Mar. 21, 2018, which is incorporated by reference in its entirety. In those embodiments, the computing device 120 can compare the volumes of geometries of anatomical structures in the MR image with historical or normative data to determine features associated with the anatomical structures. Such features can include abnormalities, increase in volumes, and reduction in volumes. The computing device 120 can be compare the findings in the radiology report with the determined features to validate or augment the findings.

Figure 2:
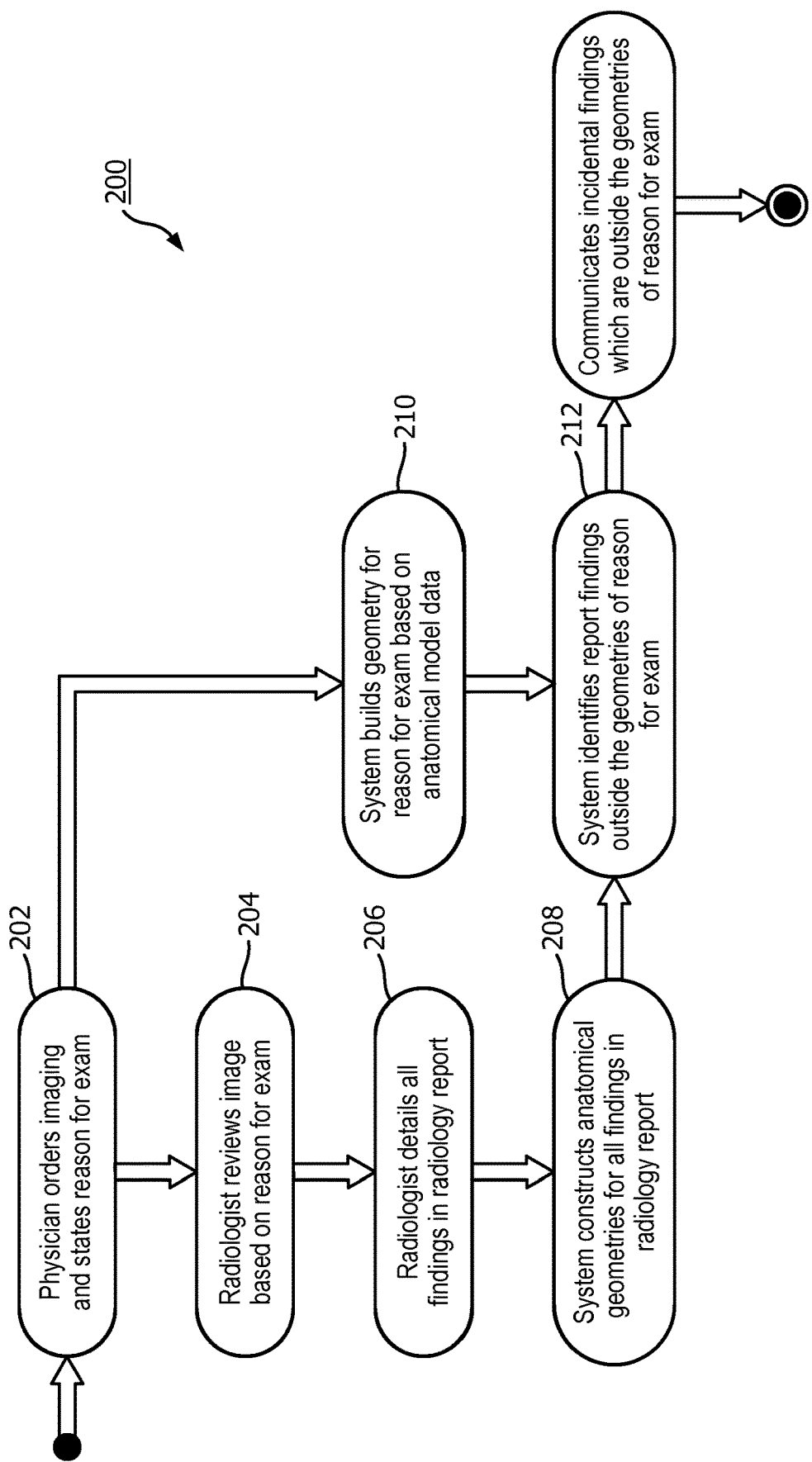
FIG. 2 is a flowchart illustrating the workflow from a physician's order of examination to the physician's receipt of actionable incidental findings, according to aspects of the present disclosure.

Referring now to FIG. 2, shown therein is a flowchart illustrating a workflow 200 that starts from a physician's order of examination to communication of the graphical representation. The workflow 200 includes activities 202, 204, 206, 208, 210, 212, and 214. The workflow 200 starts with activity 202, where the ordering physician orders the radiological imaging of a patient body and states the reason of examination (ROE). At activity 202, the ordering physician can either put the ROE in an order of radiology examination or enters the ROE at a terminal, a notebook, a computer, or a server that is connected to the computing device 120 wireless or by a cable. Before the workflow 200 proceeds to activity 204, radiological imaging, such as an MR scan, of a patient body has been taken. The radiological imaging is performed with a focus on the ROE. However, the scan can cover anatomical structures outside the ROE. The computing device 120 processes the MR data from the scan and outputs MR images to a display, such as the display device 140, for display. At activity 204, a radiologist reviews the MR images based on the reason of examination. While the ordering physician orders the radiology scan due to the ROE, the radiologist reviews the MR images for findings both within and outside of the ROE. At activity 206, the radiologist details in a radiology report all findings he/she identifies from reviewing the MR images. At activity 208 of the workflow 200, the computing device 120 of the system 100 constructs anatomical geometries concerning findings in the radiology report. At activity 208, the language engine 122 of the computing device analyzes the radiology report to identify the anatomical features associated with findings in the radiology report. The computing device 120 then segments the MR images to construct geometries of those anatomical structures. At activity 210, the system 100 builds geometries of the anatomical structures within the ROE. The computing device 120 segments the MR image based on protocols, such as 3D model constructed based on historical or normative anatomical data. At activity 212, the system 100 receives the result from the activities 208 and 210 to identify report findings outside the anatomical structures of the ROE. Finally, at activity 214, the system 100 communicates incidental findings outside the anatomical structures of the ROE. In some implementations, the system 100 communicates the incidental findings by generating a graphical representation of the incidental findings and outputting the graphical representation to the display device 140.

Figure 3:
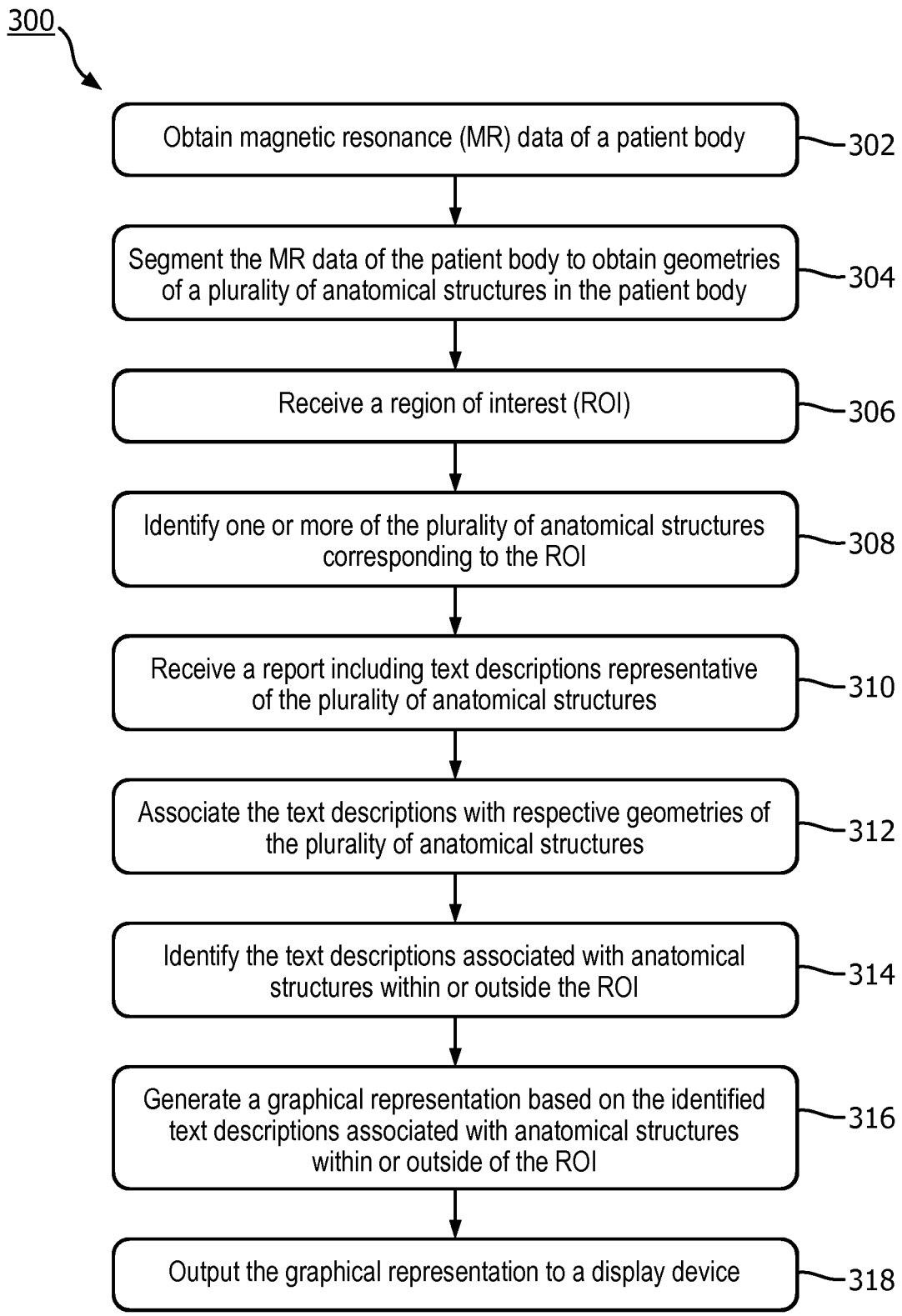
FIG. 3 is a flowchart illustrating a method of performing MR examinations, according to aspects of the present disclosure.
Figure 4:
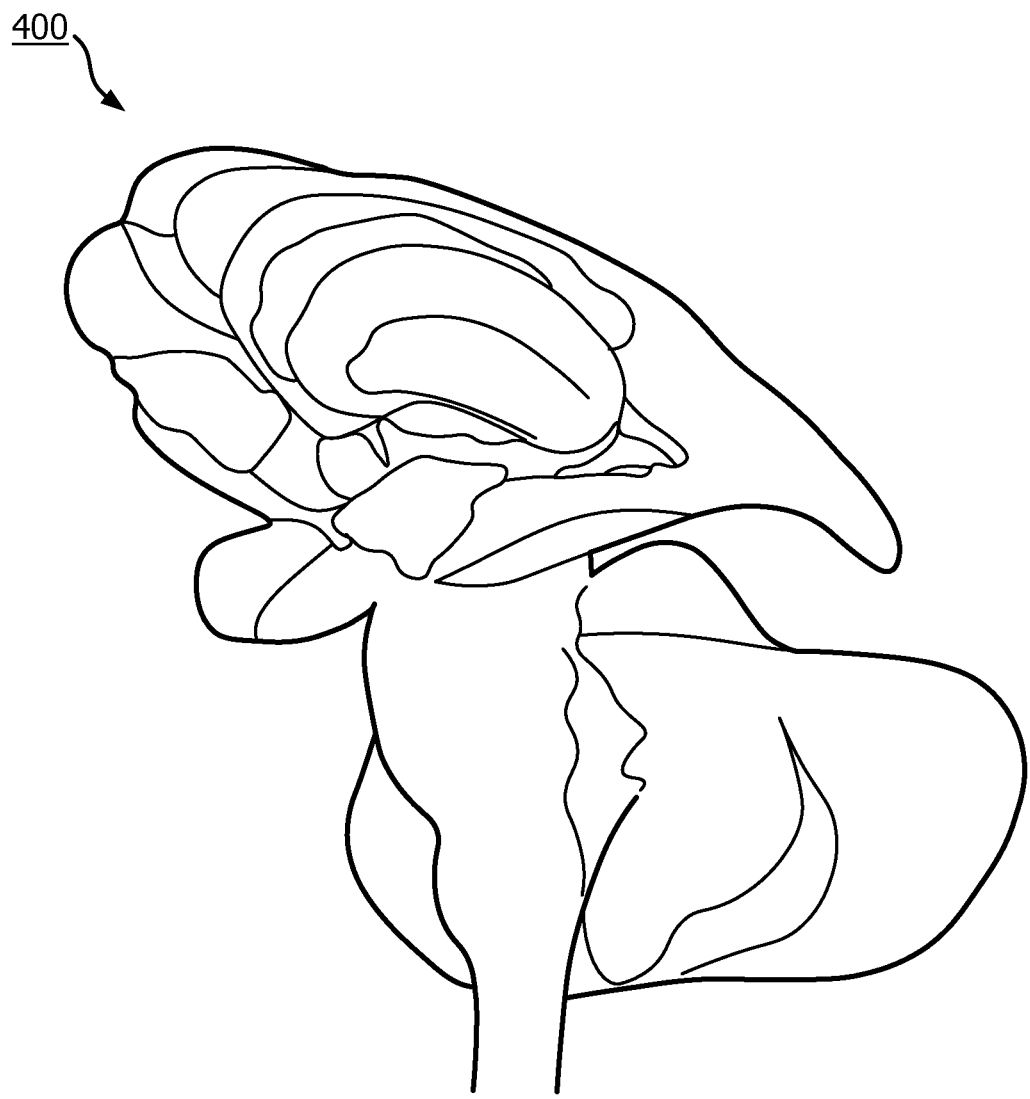
FIG. 4 is a schematic diagram of a 3D brain model of a human brain, according to aspects of the present disclosure.

FIG. 3 is a flowchart illustrating a method 300 of performing MR examinations. The method 300 includes operations 302, 304, 306, 308, 310, 312, 314, 316, and 318. It is understood that the operations of method 300 may be performed in a different order than shown in FIG. 3, additional operations can be provided before, during, and after the operations, and/or some of the operations described can be replaced or eliminated in other embodiments. The operations of the method 300 can be carried out by a computing device in a radiological imaging system, such as the computing device 120 of the system 100. The method 300 will be described below with reference to FIGS. 1, 4, 5, 6, 7 and 8.

At operation 302, MR data of a patient body is obtained by use of the MRI device 110 in communication with the computing device 120. In some embodiments, the patient body can be a part of a patient's body or an organ of a patient. For illustration purposes, the operations of the method 300 will be described based on MR examination of a patient's brain. The MR data of the patient body includes a plurality of anatomical structures. In the case of a brain, the MR data of the brain includes anatomical structures of a human brain.

Figure 5:
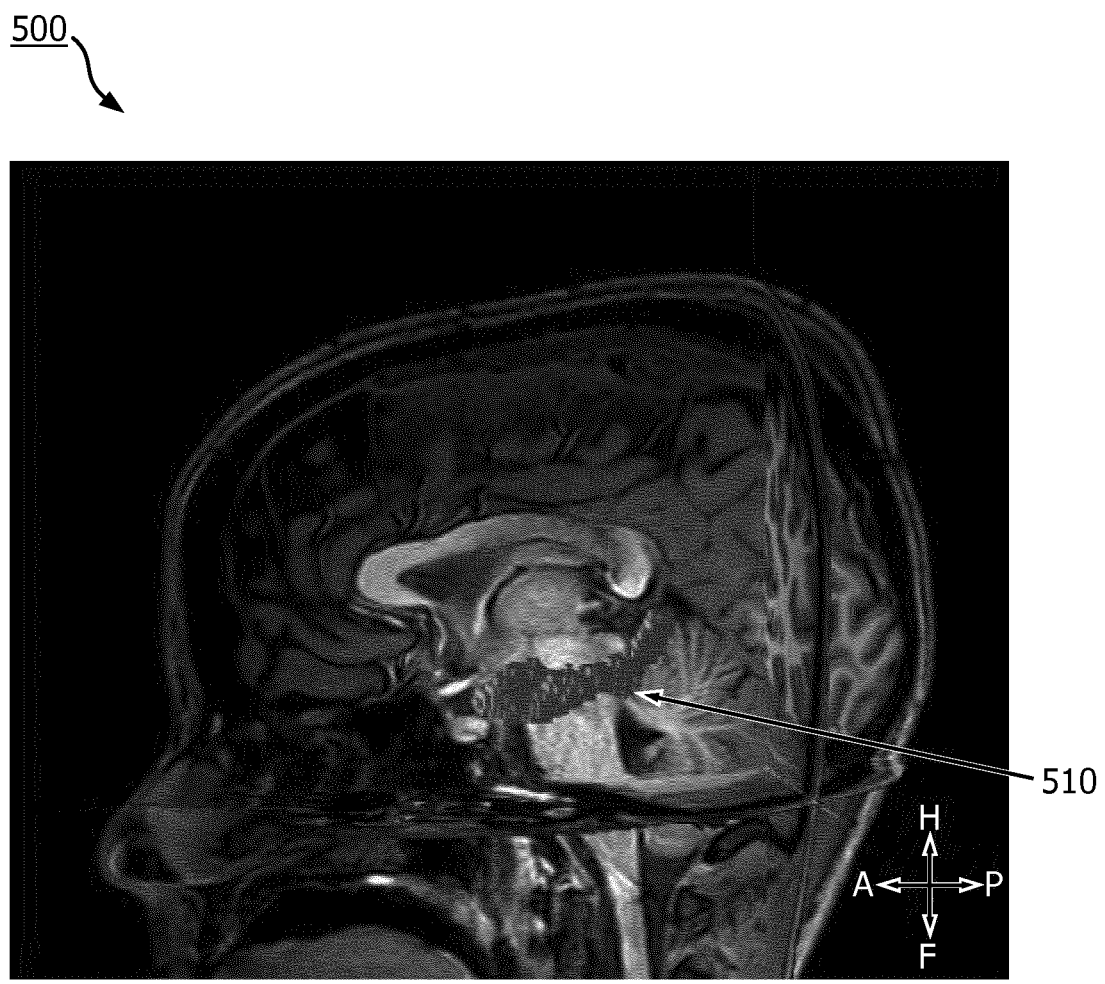
FIG. 5 is an MR image of a patient's brain overlaid with a segmented model of an anatomy, according to aspects of the present disclosure.

At operation 304, the MR data of the patient body is segmented by the imaging processor 121 of the computing device 120 to obtain geometries of the plurality of anatomical structures. In some implementations, the MR data of the patient body can be automatically segmented by the imaging processor 121 based on a segmentation protocol. In some instances, the MR data of the patient body can be automatically segmented based on a three-dimensional (3D) model of the patient body, such as the 3D brain model 400 shown in FIG. 4. In those instances, the computing device 120 of the system 100 receives a 3D brain model from a storage media or through wired or wireless connection to a server or a remote workstation. In some implementations, the 3D brain model can be stored in the database 124 or a storage device retrievable by the computing device 120. In some instances, the 3D brain model is a shape-constrained deformable brain model. In some instances, the 3D brain model may be the brain model described in "Evaluation of traumatic brain injury patients using a shape-constrained deformable model," by L. Zagorchev, C. Meyer, T. Stehle, R. Kneser, S. Young and J. Weese, 2011, in *Multimodal Brain Image Analysis* by Liu T., Shen D., Ibanez L., Tao X. (eds). MBIA 2011. *Lecture Notes in Computer Science*, vol 7012. Springer, Berlin, Heidelberg, the entirety of which is hereby incorporated by reference. In some instances, the 3D brain model may be the deformable brain model described in U.S. Pat. No. 9,256,951, titled "SYSTEM FOR RAPID AND ACCURATE QUANTITATIVE ASSESSMENT OF TRAUMATIC BRAIN INJURY" or the shape-constrained deformable brain model described in U.S. Pat. App. Pub. No. 20150146951, titled "METHOD AND SYSTEM FOR QUANTITATIVE EVALUATION OF IMAGE SEGMENTATION," each of which is hereby incorporated by reference in its entirety. The segmentation at operation 304 is exemplarily illustrated in FIG. 5. FIG. 5 shows segmentation of an amygdalahippocampal complex 510 (AHC 510) in an MR image 500. In the illustrated example, the segmentation based on a 3D brain model delineates the boundary of the AHC 510 and the geometry of the AHC 510 can be obtained.

At operation 306, the computing device 120 can receive an ROI. In some instances, the ROI can be printed in a document, such as an order for radiological examination. In those instances, the image of the document can be captured by the user input device 130, such as a camera or a scanner. To identify the ROI, the image of the document can be analyzed by the language engine 122. In some embodiments, the language engine 122 can recognize the text in the image of the document. The ROI can also be input into the computing device 120 using a different kind of the user input device 130. For example, a user, the ordering physician or a radiologist can type in the ROI on a keyboard, or pick an ROI from a drop-down menu using a mouse, touchpad, trackpad, or a touchscreen. In some other instances, the ROI is stored on a USB drive and can be received by the computing device 120 when the USB drive is plugged into the USB port. In some other implementation, the ROI is stored on a database or a server, which is connected or connectable to the computing device 120 wirelessly or by wire via communication port. In those implementations, the computing device 120 can access the ROI stored in such a database or server. In situations where in the ROI is not captured from a hardcopy document, no text recognition is necessary.

At operation 308, the language engine 122 can identify one or more of the plurality of anatomical structures corresponding to the ROI. In some embodiments, the language engine 122 can parse the radiology report to identify the text representative of anatomical structure(s) corresponding to the ROI.

At operation 310, the computing device 120 can receive a radiology report prepared by a radiologist. The radiology report includes various findings and impressions of the radiologist after he or she examines the MR images that can be displayed on the display device 140. In addition, the radiology report can include anatomical structures that are within the ROI or outside the ROI. The radiology report can be a handwritten or computer generated hardcopy or a computer readable soft copy. In implementations where the radiology report is a hardcopy, the user input device 130 can be a camera or a scanner that captures an image of the hardcopy. The language engine 122 can operate to recognize the text in the captured image of the hardcopy and convert the same into a form readable by the language engine 122. In implementations where the radiology report is a computer readable softcopy, the text recognition operation can be omitted. In some embodiments, the radiology report is generated by an interactive computer interface where the radiologist picks an anatomical structure from a pull-down list of selections and then chooses one or more findings from a pull-down list of selections. When the radiology report is generated through such an interactive computer interface, no text recognition or parsing operations are needed.

Figure 6:
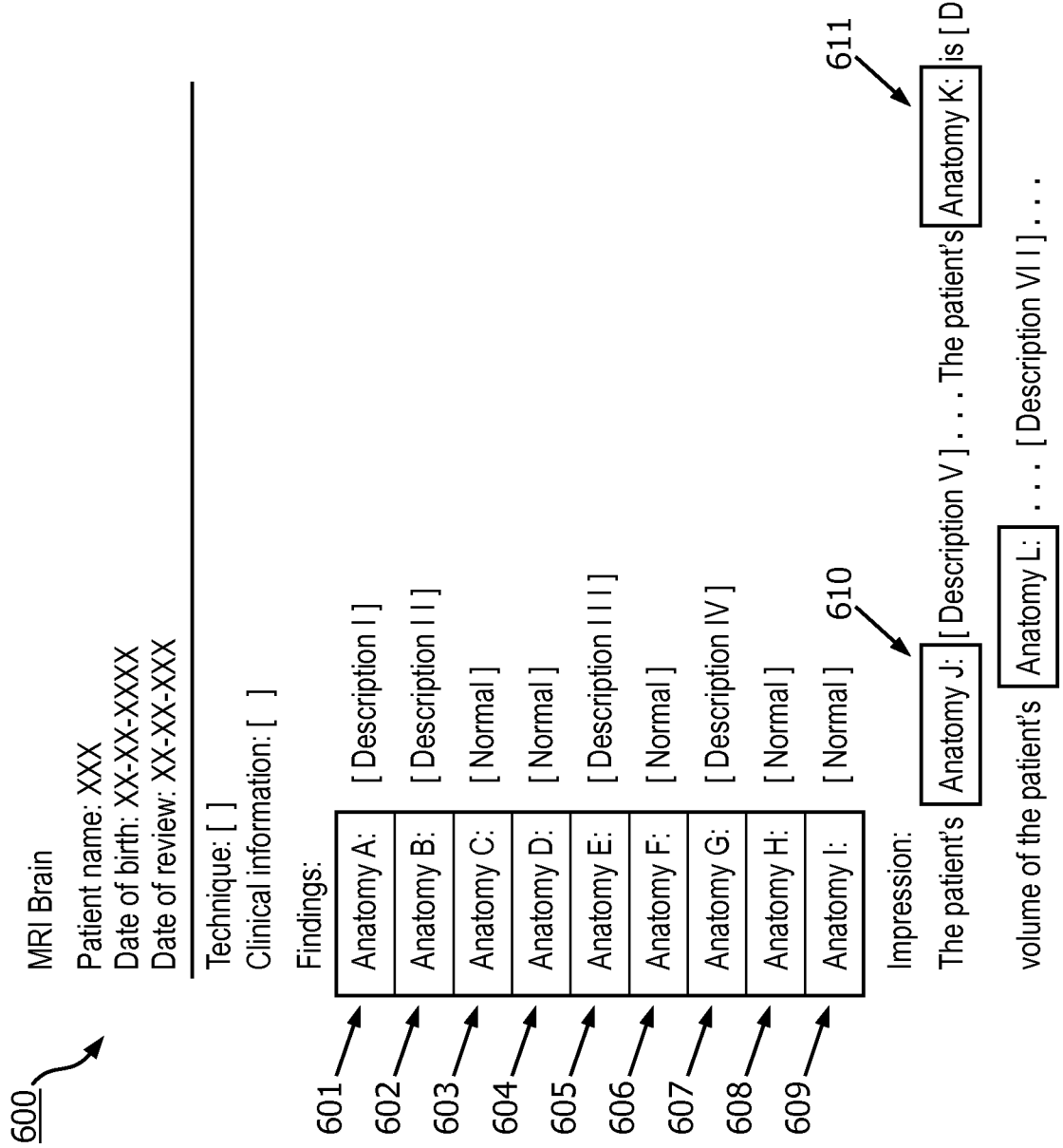
FIG. 6 is a schematic diagram of a report being analyzed for anatomical structures, according to aspects of the present disclosure.
Figure 7A:
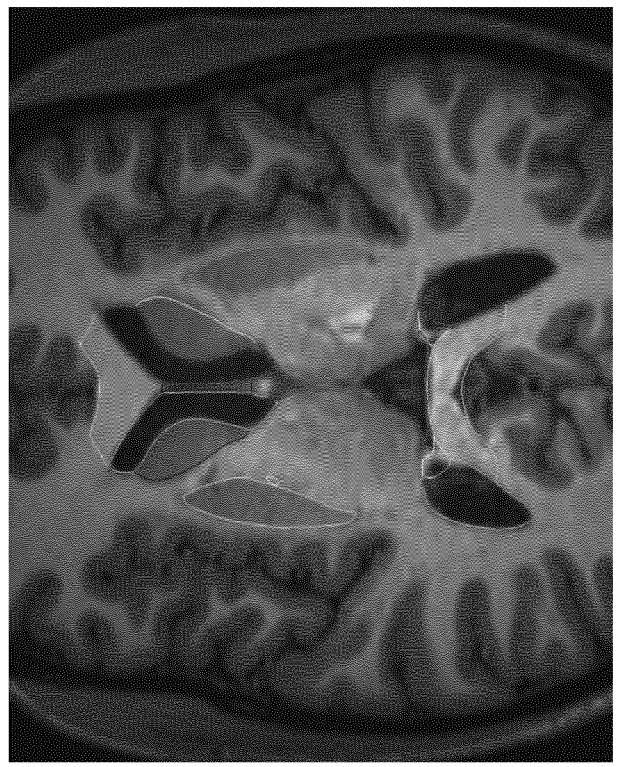
FIG. 7 is an MR image where the boundaries of anatomical structures are highlighted, according to aspects of the present disclosure.
Figure 7B:
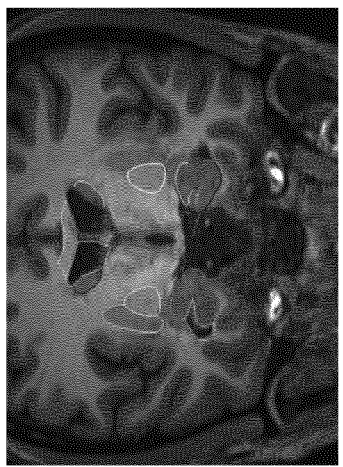
Figure 7C:

At operation 312, the text descriptions in the radiology report are associated with respective geometries of plurality of anatomical structures of the patient body. The computer readable or recognizable text as a result of operation 310 is then analyzed or parsed by the language engine 122 to associate text descriptions with anatomical structures of the patient body. Reference is now made to FIG. 6. FIG. 6 shows a schematic diagram of a radiology report 600 being analyzed for anatomical structures. Various anatomical structures (or anatomies) are identified in the "Findings" and "Impression" sections of the report. As shown in FIG. 6, Anatomy A 601, Anatomy B 602, Anatomy C 603, Anatomy D 604, Anatomy E 605, Anatomy F 606, Anatomy G 607, Anatomy H 608, and Anatomy I 609 are identified and text descriptions for these anatomical structures are associated with respective geometries of the plurality of anatomical structures.

At operation 314, the text descriptions associated with the anatomical structures within or outside the ROI are identified. The computing device 120 can compare the anatomical structures in the radiology report with the one or more anatomical structures corresponding to the ROI from operation 308. Those anatomical structures mentioned in the radiology report but not representative of the one or more anatomical structure in the ROI are outside the ROI. The computing device 120 can identify text descriptions associated with anatomical structures within the ROI and outside of the ROI.

At operation 316, the graphics engine 123 of the computing device 120 can generate a graphical representation based on the identified text descriptions associated with anatomical structures within or outside of the ROI. In some embodiments, the graphical representation can include MR images where the boundaries of geometries of anatomical structures outside the ROI are highlighted to indicate incidental findings in the radiology report. In some implementations represented by brain MR images FIGS. 7A, 7B and 7C, the graphical representation can include a side view MR image 700, a top view MR image 701, and a rear view MR image 702. In some instances, the boundaries of out-of-the-ROI anatomical structures in the radiology report are highlighted and/or colored coded. In some embodiments, the color-coded or highlighted boundaries of geometries of anatomical structures can be used to identify actionable incidental findings in the radiology report.

Figure 8:
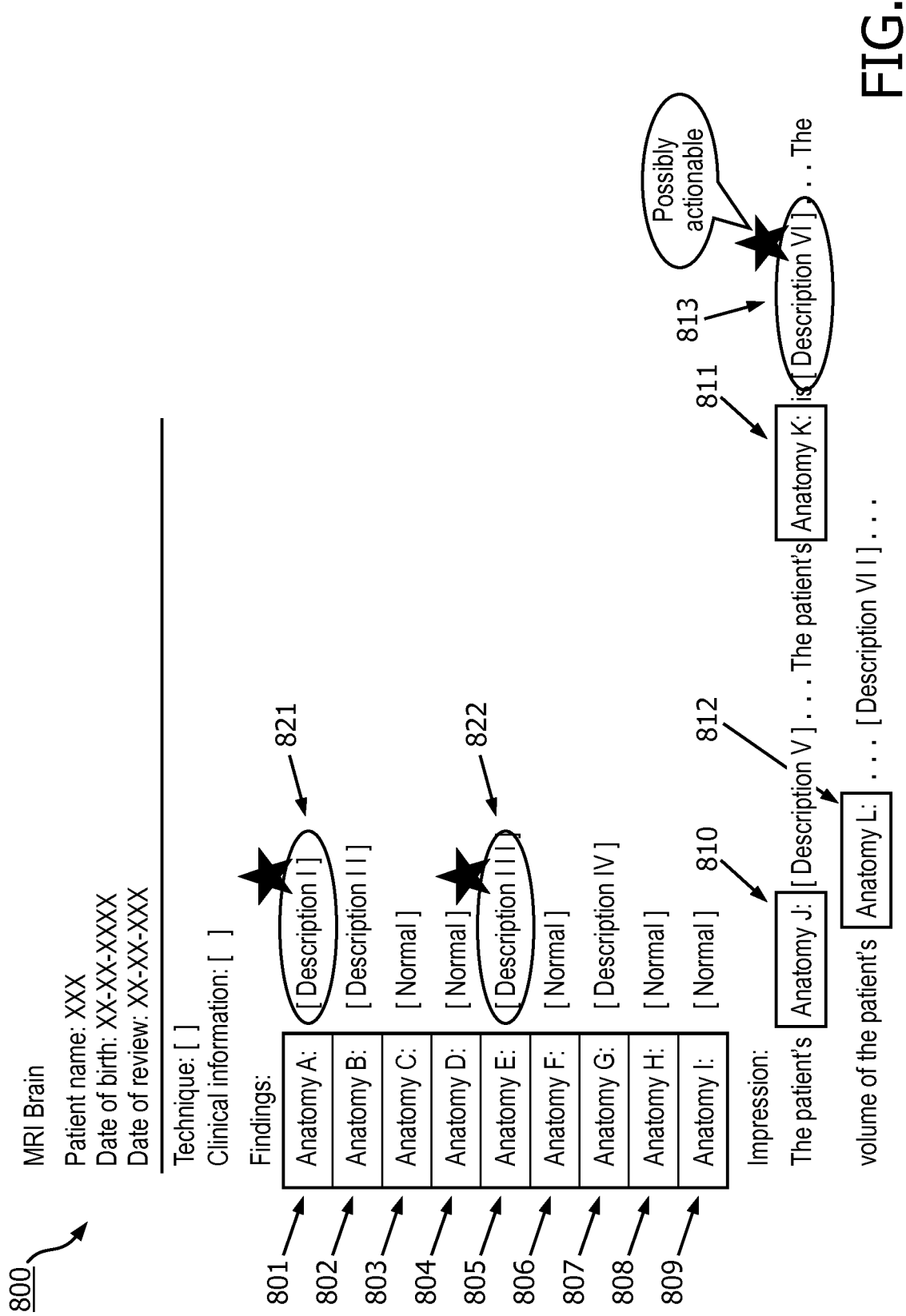
FIG. 8 is an annotated report illustrating an exemplary graphical representation of augmented incidental findings, according to aspects of the present disclosure.

In some other embodiments, the graphical representation can include an image of the radiology report with highlighted text descriptions associated with anatomical structures outside the ROI. Referring now to FIG. 8, shown therein is an image of a radiology report 800 illustrating an exemplary graphical representation of augmented incidental findings included therein. The radiology report 800 includes text descriptions associated with multiple anatomical structures—Anatomy A 801, Anatomy B 802, Anatomy C 803, Anatomy D 804, Anatomy E 805, Anatomy F 806, Anatomy G 807, Anatomy H 808, Anatomy I 809, Anatomy J 810, Anatomy K 811, and Anatomy L 812 in its "Findings" and "Impressions" sections. Out of these anatomical structures, the language engine 122 identifies Anatomy A 801, Anatomy E 805 and Anatomy K 811 as corresponding to anatomical structures within the ROI. As shown in FIG. 8, the computing device can associate Description I 821 with out-of-ROI Anatomy A 801, Description III with the out-of-ROI Anatomy E 805, and Description VI with the out-of-ROI Anatomy K 811. These text descriptions include incidental findings. The computing device 120 can highlight or otherwise indicate to a user these text descriptions. For example, the computing device 120 can overlay ovals over Description I, Description III and Description VI to highlight them. In some embodiments, the computing device 120 can overlay a star or an asterisk next to the ovals to further highlight the incidental findings of anatomical structures outside of the ROI.

In some embodiments, the database 124 of the computing device 120 stores historical and statistical data about ROI/ROE and incidental findings and/or anomalies. The historical and statistical data stored on the database 124 can be analyzed by the computing device 120 to identify probability of an incidental finding being actionable with respect to a given ROI/ROE. A finding is actionable if further examinations or tests are required or advisable to identify the cause of the finding. For example, if the structural volume of an anatomical structure deviates from the normative structural volume, which represents the expected norms, further longitudinal monitoring of patients, and/or functional imaging examinations (such as functional magnetic resonance imaging (fMRI), magnetoencephalography (MEG), electroencephalography (EEG)), and/or structural integrity examination (such as diffusion tensor imaging (DTI)). The computing device 120 can estimate the concurrence of actionable incidental findings and a given anatomical structure in the ROI/ROE. In some implementations, the computing device 120 can also take into consideration gender, race, and age of the patient such that the determination of probable concurrence of actionable incidental findings/anomalies can be more accurate. In some other implementations, the computing device 120 can access the patient's historical data, if any, stored in the database 124 to determine patient-specific probabilities of actionable incidental findings/anomalies. In some instances, the computing device 120 can store the ROI/ROE and the incidental findings in the radiology report in the database 124 for future references and analysis.

In an example illustrated in FIG. 8, the computing device 120 can access the database 124 and estimate the probabilities of concurrence of the ROI and actionable incidental findings associated with Anatomy A 801, Anatomy E 805 and Anatomy K 811. The graphics engine 123 can incorporate a clickable hyperlink or a pop-up dialogue box in the star or asterisk sign next to the oval highlighting. As shown in FIG. 8, when a user moves a cursor over the star that includes a pop-up dialogue box next to Description VI, a pop-up dialogue box shows, informing the user that the incidental finding associated with Anatomy K is possibly actionable. In some implementations, the pop-up dialogue box can include the probability of concurrence. In some embodiments, when the computing device 120 determines, based on the statistical or historical data stored in the database 124, a probability of having actionable incidental findings in an anatomical structure not addressed in the radiology report, the graphics engine 123 can include in the graphical representation an indication of possible actionable incidental findings regarding this unaddressed anatomical structure. In some implementations, if the database 124 contains information of historical actions performed or historical recommended actions to be performed in response to an actionable finding with respect to an anatomical structure, the graphics engine 123 can include in the graphical representation a recommendation of actions with respect to all possible actionable incidental findings. Actionable findings can include medical diagnostic and/or treatment procedures associated with the one or more anatomical structure.

In some implementations, the graphical representation can include a list of anatomical structures outside the ROI and associated text descriptions. In some other implementations, the graphical representation can include a table of anatomical structures outside the ROI and associated text descriptions. Referring now to FIG. 9, shown therein is a table 900 as an exemplary form of graphical representation according to the present disclosure. The table 900 includes five columns- "Regions outside ROE," "Report Findings," "Alert," "% of Concurrence," and "Recommended Actions." In the "Regions outside ROE" column, the table 900 lists all out-of-ROE anatomical structures identified by the computing device 120. The "Report Findings" column of the table is populated by text descriptions associated with each of the out-of-ROE anatomical structures in the "Regions outside ROE" column. The "Alert" column is populated with indication of possible actionable findings as a result of the computing device 120's estimation based on the statistical and/or historical data in the database 124. As shown in the table 900, even though the radiology report is silent on Anatomy O, graphics engine 123 can include in the table 900 an alert indicating a possible actionable finding of Anatomy O based on statistical or historical data. In the "% of concurrence" column, the table 900 shows the estimated percentage of concurrence with the ROE for each of the possible actionable finding in the "Alert" column. In some implementations, the table 900 can also include the "Recommended Actions" column if the database 124 contains data concerning historical actions performed or historical recommended actions for the possible actionable findings in the "Alert" column.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method for magnetic resonance (MR) examination, the method comprising:

receiving, at a computing device in communication with a magnetic resonance imaging (MRI) device, MR data of a patient body comprising a plurality of anatomical structures, the plurality of anatomical structures including a region of interest;

segmenting, by the computing device, the MR data to obtain geometries of the plurality of anatomical structures;

receiving, at the computing device, a report comprising text descriptions representative of the plurality of anatomical structures;

associating, by the computing device, the text descriptions with respective geometries of the plurality of anatomical structures;

identifying, by the computing device, the text descriptions associated with anatomical structures within or outside of the region of interest, wherein the text descriptions associated with the anatomical structures outside of the region of interest comprise an actionable finding associated with an anatomic structure outside the region of interest;

obtaining a probability of concurrence of one or more of the actionable findings associated with respective anatomical structure outside the region of interest and the region of interest so designated; and outputting, by the computing device, a graphical representation based on the identified text descriptions associated with anatomical structures within or outside of the region of interest.

2. The method of claim 1, wherein the graphical representation comprises highlighted boundaries of geometries of anatomical structures outside the region of interest.

3. The method of claim 1, wherein associating the text descriptions with respective geometries of the plurality of anatomical structures comprises parsing the text descriptions.

4. The method of claim 1, wherein associating the text descriptions with respective geometries of the plurality of anatomical structures comprises recognizing text in the report.

5. The method of claim 1, further comprising storing in a database the region of interest and the actionable finding associated with the anatomic structure outside the region of interest.

6. The method of claim 1, wherein the graphical representation comprises the probability of concurrence of the actionable finding associated with the anatomic structure outside of the region of interest and the region of interest being so designated.

7. The method of claim 1, wherein the graphical representation comprises a recommendation of actions based on the probability of concurrence of the actionable finding associated with the anatomic structure outside of the region of interest and the region of interest being so designated.

8. A magnetic resonance (MR) examination system, comprising a computing device in communication with a magnetic resonance imaging (MRI) device, the computing device operable to:
receive, from the MRI device, MR data of a patient body comprising a plurality of anatomical structures, the plurality of anatomical structures including a region of interest;
segment the MR data to obtain geometries of the plurality of anatomical structures;
receive a report comprising text descriptions representative of the patient body;
associate the text descriptions with respective geometries of the plurality of anatomical structures;
identify the text descriptions associated with anatomical structures within or and outside of the region of interest, wherein the text descriptions associated with the anatomical structures outside of the region of interest comprise an actionable finding associated with an anatomic structure outside the region of interest;
obtain a probability of concurrence of one or more of the actionable findings associated with respective anatomical structure outside the region of interest and the region of interest so designated; and
output, to a display device, a graphical representation based on the identified text descriptions associated with anatomical structures within or and outside of the region of interest.

9. The system of claim 8, furthering comprising the MRI device.

10. The system of claim 8, furthering comprising the display device.

11. The system of claim 8, wherein the computing device is further operable to store in a database the region of interest and the actionable finding associated with the anatomic structure outside the region of interest.

12. The system of claim 8, wherein the graphical representation comprises the probability of concurrence of the actionable finding associated with the anatomic structure outside of the region of interest and the region of interest being so designated.

13. The system of claim 8, wherein the graphical representation comprises a recommendation of actions based on the probability of concurrence of the actionable finding associated with the anatomic structure outside of the region of interest and the region of interest being so designated.

14. A non-transitory computer readable medium having instructions thereon that cause a computing device to:
receive segmented magnetic resonance (MR) data including geometries of a plurality of anatomical structures;
receive a report comprising text descriptions representative of a patient body;
associate the text descriptions with respective geometries of the plurality of anatomical structures;
identify the text descriptions associated with anatomical structures within or and outside of the region of interest, wherein the text descriptions associated with the anatomical structures outside of the region of interest comprise an actionable finding associated with an anatomic structure outside the region of interest;
obtain a probability of concurrence of one or more of the actionable findings associated with respective anatomical structure outside the region of interest and the region of interest so designated; and
output, to a display device, a graphical representation based on the identified text descriptions associated with anatomical structures within or and outside of the region of interest.

* * * * *